(12) United States Patent
Cozzi et al.

(10) Patent No.: US 7,411,111 B2
(45) Date of Patent: Aug. 12, 2008

(54) METHOD FOR CLONING OF THE RAT BY NUCLEAR TRANSFER

(75) Inventors: Jean Cozzi, Lyons (FR); Qi Zhou, Beijing (CN); Jean-Paul Renard, Vanves (FR)

(73) Assignee: Institut National de la Recherche Agronomique, Paris (FR)

( * ) Notice: Subject to any disclaimer, the term of this patent is extended or adjusted under 35 U.S.C. 154(b) by 76 days.

(21) Appl. No.: 10/556,873

(22) PCT Filed: May 24, 2004

(86) PCT No.: PCT/FR2004/001275

§ 371 (c)(1),
(2), (4) Date: Nov. 15, 2005

(87) PCT Pub. No.: WO2004/105477

PCT Pub. Date: Dec. 9, 2004

(65) Prior Publication Data

US 2006/0277616 A1    Dec. 7, 2006

(30) Foreign Application Priority Data

May 23, 2003  (FR)  .................................. 03 06223

(51) Int. Cl.
*A01K 67/00*  (2006.01)
*C12N 15/00*  (2006.01)

(52) U.S. Cl. .......................................... 800/14; 800/24
(58) Field of Classification Search .................. 800/24, 800/8, 14
See application file for complete search history.

(56) References Cited

OTHER PUBLICATIONS

Oller do Nascimento et al. Evidence for Conservationo of Dietary Lipid in the Rat During Lactation and the Immediate Period After Removal of the Litter. Biochem. J., 1986, vol. 239, pp. 233-236.*
Campbellm K.H.S. Nuclear Equivalence, Nuclear Transfer and the Cell Cycle (1999) Cloning, vol. 1, pp. 3-15.*
Dinnyes et al. Parthenogenic Activation of Porcine Oocytes by Electric Pulse and/or Butyrolactone I Treatment. Cloning. 2000/1999, vol. 1, pp. 209-216.*
Hayes et al. (2001) *Physiol. Genomics* 5:193-203.
Hirabayashi et al. (2003) *J. Reprod. Dev.* 49:121-126.
Iannaccone et al. (2001) *Zygote* 9:135-143.
Josefsberg et al. (2000) *Biol. Reprod.* 62:1270-1277.
Lee et al. (1998) *Trends in Cell Biology* 8:397-403.
Zernieka-Goetz (1991) *Molecular Reproduction and Development* 18:169-176.
Zhou et al. (2003) *Science* 302:1179.

* cited by examiner

*Primary Examiner*—Deborah Crouch
(74) *Attorney, Agent, or Firm*—Colin L. Fairman; Dorsey & Whitney LLP

(57) ABSTRACT

The invention relates to a method for cloning in the rat by nuclear transfer. The invention further relates to the rats obtained thus, in the foetal or adult state, as well as use thereof for the production of molecules of interest or as study models.

38 Claims, No Drawings

METHOD FOR CLONING OF THE RAT BY NUCLEAR TRANSFER

This invention relates to a method for cloning of the rat by nuclear transfer. The invention also relates to the rats thus obtained, as well as to their use for the production of molecules of interest or as models for study.

Associated with a genetic modification of the cells before their use as a source of nuclei, the technology of nuclear transfer makes possible the establishment of lines of animals genetically modified for specific characteristics. The techniques of nuclear transfer are well known and were developed for the cloning of several animal species, in particular of mammals, such as the sheep (Wilmut et al., 1997; WO 97 07669), the mouse (Wakayama et al., 1998; WO 99 37143), cattle (Wells et al., 1999), the goat (Baguisi et al., 1999; WO 00 25578), the pig (Polejaeva et al., 2000) and the rabbit (Chesne et al., 2002). The methods of nuclear transfer are described in particular by Campbell & al. (*Nuclear transfer in practice*, School of Biosciences, University of Nottingham, Leicestershire, United Kingdom).

These methods of nuclear transfer generally comprise the following steps of:

a) removal of an ovocyte and its maintenance in an appropriate culture medium;

b) enucleation of this ovocyte, i.e., removal by micromanipulation of its nucleus then in metaphase form;

c) insertion of a nucleus of a foetal or adult somatic cell or of an embryonic cell or of a cell of the germinal line in the reconstituted enucleated ovocyte (nuclear transfer);

d) activation of the reconstituted ovocyte obtained in step c) in order to obtain a reconstituted embryo.

The reconstituted embryo is then either implanted in a recipient female so that it might develop, possibly into a foetus and then into a neonate, or is cultured in vitro during the initial stages of its pre-implantational development before being placed in the oviduct or uterus of a recipient female.

The stage of the cell cycle reached by the ovocyte at the time of its harvest and its capacity to be maintained at this stage until the time of the transfer of the nucleus is a limiting factor in making possible not only the effective enucleation of the ovocyte but also the synchronisation between the cell cycles of the recipient ovocyte and the exogenous nucleus and consequently the production of an embryo and its development to term.

Nuclear transfer in the ovocytes of rats has already been described in the scientific literature (Iannacone & al., 2001; Hayes & al., 2001; Hirabayashi & al., 2003; Hirabayashi & al., 2003). However, no nuclear transfer making possible the development of an implanted embryo has been reported, nor has obviously the development of a rat foetus and then of a neonate from these reconstituted ovocytes.

The method of cloning according to the invention is the first reported which has made possible the production of reconstituted rat ovocytes capable of developing into viable foetuses, and consequently into living rats whose fertility could be verified.

Until now, in vitro maintenance of ovocytes in the "non-activated" state, i.e., at the stage of the second meiotic division was ensured in mammals and in particular in the rat by rapid removal of the oviducts outside the sacrificed animal and then the preparation and in vitro maintenance of the ovocytes in an appropriate environment (temperature, pH, calcium) (exposure to a culture medium devoid of calcium, for example) which only slows the evolution of the ovocyte activation process. This process, which is triggered under natural conditions by the spermatozoon, is characterised by a pulsatile release of calcium ions stored in endoplasmic vesicles leading to an abrupt reduction in the activity of the MPF factor (Maturation Promoting Factor), a protein complex characterised by the association of cyclin B and an enzyme kinase (cdc2), by proteolytic degradation of the cyclins involved. The major disadvantages of the approaches used to date and cited previously for maintenance of the ovocyte at the metaphase stage of the second meiotic division are, on the one hand, the impossibility of effectively inhibiting the in vitro biochemical development of the ovocyte and, on the other hand, maintaining the ovocyte in a physiological state making it possible for it to withstand the mechanical constraints of the micromanipulation. As a matter of fact, this biochemical development rapidly becomes unfavourable in the case of transfer of nuclei after enucleation of the ovocyte (cloning) because it rapidly leads to the appearance of a high membrane fragility of the ovocyte and therefore to its more frequent lysis after micromanipulation, and especially to a reduction of the potential for development of the reconstituted embryo, because its nucleus then rapidly undergoes alterations inherent in the entry into interphase which accompanies the triggering of the activation process. The activation process, when it occurs spontaneously before the transfer of the nucleus, can have 2 unfavourable consequences for the re-programming of the exogenous nucleus:

at first, very rapid deformations of the chromatin which is exposed from the time of its introduction into the ovocyte to the dynamic process of decondensation which leads to numerous structural alterations and the formation of several micro-nuclei;

and then, the exposure of the nucleus to a cytoplasmic environment in which factors required for reprogramming are degraded, preventing the formation of a functional nucleus.

Although these factors are not known, their importance is clearly demonstrated by the fact that no reprogramming can be obtained when the nucleus is introduced into an egg at the one cell stage (therefore already activated) and enucleated.

The method according to the invention makes possible the in vitro maintenance of the ovocyte in a physiologically stable state for several hours after its collection from the oviduct and thus prevents the spontaneous activation in vitro of the ovocyte observed in many species but more particularly in the rat (Zernicka-Goetz, 1990). It makes it possible to expose the exogenous nucleus to a cytoplasmic environment which promotes the organisation of its chromatin into a metaphase-type structure similar to that of the nucleus of the ovocyte for which it was substituted. The method according to the invention may also comprise a rapid technique for reconstruction of the embryo propitious to its reactivation by making it possible (i) to reduce the time of exposure of the ovocyte to the compounds which prevent its activation and (ii) to increase the time of exposure of the exogenous chromatin to the ovocyte factors involved in the functional reprogramming of a nucleus that are still present and/or functional in the cytoplasm before activation.

This invention therefore relates to a method for the production of rat embryos reconstituted by nuclear transfer comprising the following steps:

a) removal of an ovocyte from a female rat and maintenance in an appropriate medium;

b) insertion of a nucleus from a rat cell into the recipient rat ovocyte previously maintained in vitro in order to obtain a reconstituted ovocyte (nuclear transfer);

c) activation of the reconstituted ovocyte obtained in step b) in order to obtain a reconstituted embryo;

characterised in that the recipient rat ovocyte removed is maintained at the metaphase stage of the second meiotic division through maintenance in an appropriate medium including a reversible proteasome inhibitor (maintenance medium), and in that the reconstituted ovocyte is activated by exposure to an appropriate medium containing an activation inducer (activation medium).

The appropriate media for the in vitro maintenance and/or for activation of ovocytes, in particular rat ovocytes, are well known by those skilled in the art, described in particular in the references previously cited as well as by Miyoshi et al. (1997, Stage dependant development of rat 1-cell embryos in a chemically defined medium after fertilization in vivo and in vitro. Biol. Reprod.; 56: 180-185).

The reversible proteasome inhibitors are also known by those skilled in the art, described in particular by Hee Lee & Goldberg (*Proteasome inhibitors: valuable new tools for cell biologists*, Trends in Cell Biology (Vol. 8), October 1998). They are to best advantage chosen from among peptide aldehyde Cbz-LLL-H (MG132), peptide boronate Cbz-LLL-B (OH)2, vinyl sulfone Cbz-LLL-Vs, lactacystine and beta-lactone, leupeptine, MG101, MG115, MG262 and PSI (Cbz-ile-glu), preferably MG132.

Without prejudging their mode of functionality, the reversible character of action of some proteasome inhibitors can be obtained by limiting the exposure time to these proteasome inhibitors of the recipient ovocytes harvested and maintained in vitro.

The maximum exposure time during which the harvested ovocytes can be maintained in vitro in the metaphase stage of the second meiotic division without losing their capacity to be activated for the development of embryos, and then of foetuses and finally of viable neonate rats, can be determined experimentally by those skilled in the art.

Preferentially, this exposure time of the recipient ovocyte to the reversible proteasome inhibitor in the maintenance medium is less than 8 hours, preferably between 1 and 6 hours.

The quantity of reversible proteasome inhibitor in the maintenance medium for the recipient ovocyte will be determined by those skilled in the art as a function of the specific properties of each inhibitor, in such a way that it will make possible the reversible maintenance of the ovocyte at the metaphase stage of second meiosis. The concentration of this inhibitor in the maintenance medium will preferably be between 1 and 10 µM.

For nuclear transfer step b), the culture medium for the recipient ovocyte is substantially free of reversible proteasome inhibitor. This makes it possible to avoid exposure of the nucleus donor cells to the action of said inhibitors and a potential negative effect on the capacity of the reconstituted ovocytes for subsequently developing functional embryos, and then functional foetuses and neonates.

The nuclear transfer generally includes a step for removal of the nucleus of the recipient ovocyte, followed by a step for introduction of the donor cell nucleus into the enucleated ovocyte.

According to a preferential embodiment of the invention, the nuclear transfer includes a step for introduction of the donor cell nucleus into the recipient ovocyte followed by a step for removal of the nucleus of the recipient ovocyte.

Transfer of the donor cell nucleus into the cytoplasm of the recipient ovocyte is preferentially done by micro-injection. Removal of the recipient ovocyte nucleus is preferentially done by micropipetting.

According to a more preferential embodiment of the invention, the nuclear transfer is done by micro-injection with rapid reconstruction of the ovocyte in a single step.

Conventional techniques of embryo reconstruction generally proceed in 2 steps. They consist in the first place in enucleating the ovocyte and then in incorporating the desired nucleus in the enucleated cytoplasm by micro-injection or electrofusion. The method according to the invention consists in at first injecting, preferentially by means of a piezoelectric system, the denuded nucleus of the donor cell from the side opposite to the ovocyte metaphase; and then subsequently in withdrawing the ovocyte metaphase by negative pressure at the time of withdrawal of the injection pipette, the latter being extracted out of the cytoplasm with a little of the plasma membrane at the entry site of the pipette. This method makes it possible for the plasma membrane to seal itself at the break-in site of the pipette, thus considerably limiting ovocyte lysis. The embryo is therefore reconstructed in a very short time, in this way avoiding a premature ovocyte activation, prior to transfer of the nucleus.

For step c) of the method according to the invention, the activation medium is to best advantage substantially free from reversible proteasome inhibitor.

Activation inducers for reconstituted ovocytes are well known by those skilled in the art, described in particular by Hardcastle & al. (*Designing Inhibitors of Cyclin-Dependant Linases*, Annu. Rev. Pharmacol. Toxicol. 2002, 42:325-48). According to a preferential embodiment of the invention, the activation inducer is butyrolactone-1.

The quantity of activation inducer in the culture medium of the reconstituted ovocyte will be determined by those skilled in the art as a function of the specific properties of each activator. For butyrolactone-1, the concentration of this inhibitor in the culture medium will preferably be between 25 and 150 µM.

The donor cell according to the invention may be any cell type that contains a genome or genetic material, such as somatic cells, germinal cells, embryonic cells such as pluripotent stem cells, totipotent stem cells, like embryonic stem cells for example (ES cells). The term "somatic cell" refers to differentiated diploid cells. The somatic cell can equally well come from an animal, or from a culture of cells or tissues that have undergone at least one passage in culture and that have or have not been frozen. When the somatic cell is derived from an animal, the animal may be at any stage of development, for example an embryo, a foetus or an adult.

The somatic cells include, preferably and in a non-restrictive way, fibroblasts (for example, primary fibroblasts), epithelial cells, muscle cells, cumulus cells, neural cells, mammary cells, hepatocytes, Langerhans cells, cells derived from the three germ layers which make possible the formation of an organism in ecto, meso and endoderm. Preferably, the donor somatic cells are foetal fibroblasts. The somatic cells can be obtained, for example, by dissociation of tissues by mechanical or enzymatic means (in general by use of trypsin or proteases) in order to obtain a cell suspension that is in general cultured until a confluent cell monolayer is obtained. The somatic cells may be harvested or prepared for cryopreservation and kept frozen for later use. The nuclei donor cells are equally well in the proliferative state or the quiescent state. The quiescent state which corresponds to the Go/G1 stage of the cell cycle is obtained in culture cells by contact inhibition or by serum deprivation (Whitfield et al., 1985) or by cell cycle inhibitors (Kues WA et al., 2002, Cell cycle synchronisation of porcine foetal fibroblasts: effect of serum deprivation and reversible cell inhibitors). The proliferative state may be considered as corresponding to all other stages of the cell cycle.

Preferentially, the donor cell nucleus is removed for its insertion into the recipient ovocyte when its chromatin is in mitosis.

To best advantage, the reconstituted embryo is implanted in the oviduct or uterus of a recipient female and said transferred embryo is allowed to become implanted and develop in the uterus of said recipient female.

The techniques for transfer of reconstituted embryos into the uteri of recipient females are well known to those skilled in the art.

According to a particular embodiment of the invention, the reconstituted embryo is transferred at the 1 cell stage.

According to another particular embodiment of the invention, the reconstituted embryo is transferred at the 2 cell stage.

Once transferred, the embryo will develop to best advantage into a foetus, and then into a neonate.

This invention therefore also relates to a rat embryo, and/or foetus, neonate, adult rat, or cells derived from them, produced by a method comprising or including the process previously described.

The invention also relates to the progenies of adult rats produced by a method comprising or including the process according to the invention previously described.

The invention also relates to an in vitro method for the cloning of rats by nuclear transfer comprising or including a method according to the invention previously described.

According to a particular embodiment of the invention, the donor cells may also have been genetically manipulated in particular by the positive or negative deregulation of a gene or by integration of a heterologous gene. The techniques of genetic manipulation of mammalian cells are well known to those skilled in the art.

According to a particular embodiment of the invention, the reconstituted embryo is therefore a transgenic embryo.

The transgene, i.e., the heterologous nucleic acid integrated in the genome of the rat donor cell is not limited to a particular DNA sequence. It might be a sequence coding for a heterologous protein, or a sequence coding for an RNA capable of blocking the translation of an RNA produced by an endogenous gene, such as for example an anti-sense RNA. The nucleic acid sequence of the transgene, in particular of DNA, may be of a purely synthetic origin (for example routinely constructed by a DNA synthesizer), or may be derived from mRNA sequences by reverse transcription, or may be directly derived from genomic DNA sequences. When the DNA sequence is derived from RNA sequences by reverse transcription, this may or may not contain all or part of non-coding sequences such as introns, according to whether the corresponding RNA molecule has or has not undergone, partially or totally, a splicing. The transgene may be as small as a few hundred base pairs of cDNA or as large as a hundred thousand of base pairs of a gene locus comprising the exon-intron coding sequence and the regulatory sequences required to obtain a spatially-temporally controlled expression. The segment of recombinant DNA may have a size between 2.5 kb and 1,000 kb. The recombinant DNA segment can also be less than 2.5 kb or greater than 1,000 kb, making possible a transgenesis by Yac (Pook MA & al. 2001).

The transgene or DNA sequence of this invention is preferably in the native form, i.e., derived directly from an exogenous DNA sequence naturally present in an animal cell. This DNA sequence in the native form may be modified for example by insertion of restriction sites required for cloning and/or by insertion of site-specific recombination sites (lox and flp sequences). Alternatively, the DNA sequence of this invention may have been artificially created in vitro by chemical synthesis or by recombinant DNA techniques, by associating for example portions of genomic DNA and cDNA.

The transgene preferably contains appropriate regulatory sequences for directing and controlling the expression of genes coding for said polypeptides in the appropriate cell type(s). By elements controlling gene expression, we understand the designation of all nucleic acid sequences involved in the regulation of gene expression, i.e., essentially the regulatory sequences of transcription, splicing and translation. Among the regulatory sequences for transcription, the minimal promoter sequence, the upstream sequences (for example, the SP1 box, the IRE for "interferon responsive element," etc.), the activator sequences ("enhancers"), possibly the inhibitor sequences ("silencers"), the insulator sequences ("insulators"), and the splicing sequences should be mentioned. The elements controlling gene expression make possible either an expression that is constitutive, ubiquitous, inducible, specific to a cell type ("tissue-specific") or specific to a developmental stage. These elements may or may not be heterologous to the organism, or be naturally present or not in the organism's genome. It is obvious that in terms of the sought-after result, those skilled in the art will choose and adapt the regulatory elements for gene expression. In order to direct the expression of the transgene in an animal's biological fluid, such as the milk, the transcription regulatory sequence used is selected from the promoter sequences of the genes specifically active in the cells secreting these biological fluids, such as the cells of the mammary glands for example in order to direct expression in the milk. Among the preferred biological fluids, milk, blood, sperm and urine should be mentioned.

Use of a transgenic cloned rat according to the invention for the production of recombinant proteins of interest is an object of this invention. The recombinant protein of interest may be any protein, for example a therapeutic protein such as α-, β-, δ-globin, blood coagulation factors (factors VIII and IX), cell surface receptors, antibodies, enzymes, etc., and other proteins required to for example correct inherited or acquired defects in a patient.

The invention also relates to the use of a cloned rat according to the invention, in particular a transgenic cloned rat according to the invention, as a model for the study of human pathologies. By way of example of human pathologies, mucoviscidosis, atherosclerosis, cancer, metabolic diseases and ocular pathologies should be mentioned. Cloned rats according to the invention may also be employed in any neurobiological study or in behavioural models.

To best advantage, the recipient ovocytes and/or the donor cells originate from rat lines chosen from among consanguine lines, hybrid lines and so-called non-consanguine "outbred" lines. Preferably, the recipient ovocytes and/or donor cells originate from non-consanguine "outbred" lines, such as for example the Sprague-Dawley or Wistar lines.

The method according to the invention presents the advantage of strictly and reversibly controlling the ovodyte activation process by acting upstream of the biochemical processes that control activation and by preventing the degradation of the macromolecular compounds responsible for arrest of the ovocyte in metaphase and in particular of the cyclins. In order to do this, the ovocyte is exposed in vitro to one or more inhibitor(s) of proteasome, a key organelle of the cell: inhibition of its proteolytic action on the cyclins makes it possible to maintain an elevated level of MPF kinasic activity which determines metaphase arrest. The majority of ovocytes may thus be maintained in metaphase of the second meiotic division for several hours after their harvest (table 1).

TABLE 1

Inhibition of spontaneous activation of rat ovocytes by exposure to a proteasome inhibitor (MG132)
% of activated ovocytes after collection (t = 0)

|  | t = 0 | t = 210 m |
|---|---|---|
| MG132 | 0% (0/68) | 33.8% (23/68) |
| Control | 0% (0/46) | 76.1% (35/46) |

Repeats, n = 2

When the inhibitor is removed, the activation mechanisms can be triggered, the ovocyte expels the second polar body and can initiate a normal development (table 2).

TABLE 2

Reversibility of the inhibition of the spontaneous activation of rat ovocytes after their exposure to a proteasome inhibitor (MG132) for 120 min.
% of embryos (parthenogenetic development at the morula stage) obtained after removal of MG132 and induction of the activation process by butyrolactone

| t = 0 removal of MG132 | t = 120 min |
|---|---|
| 0% (0/71) | 45.9% (34/74) |

Repeats, n = 5

The ovocytes keep their mechanical properties with respect to micromanipulation which makes possible the effective routine realisation of the operations required for the transfer of nuclei (table 3).

TABLE 3

Cleavage of rat embryos reconstructed by nuclear transfer after removal of MG132 followed by exposure to BLI
% of embryos at the 2 cell stage 24 hr after removal of BLI

| Control* | 66.5% (117/176) |
|---|---|
| MG132** | 89.2% (166/18) |

*repeats = 4;
**repeats = 3

By the method according to the invention, the ovocytes are transferred to a medium not containing inhibitor(s) right before conducting the reconstruction of the embryos. This makes it possible to avoid direct exposure of the nucleus donor cells to their action. Reconstruction of the embryos must then be carried out very rapidly before proteasome becomes functional again in order to avoid a premature activation of the ovocyte. The purpose of this rapid reconstruction is to lengthen the period during which the condensed chromatin of the nucleus is directly exposed to the ovocyte factors which make possible the reprogramming of the activity of the foreign nucleus. It then becomes possible to reconstitute a greater number of embryos during a given time period, and therefore to increase the number of transplanted embryos per recipient female for in vivo development. This possibility makes it possible to get around the low rate of implantation observed in the rat after transfer of a nucleus (table 4)

TABLE 4

Rate of foetal development of rat embryos reconstructed from ovocytes previously exposed to a proteasome inhibitor (MG132)

| treatment | pregnant recipients between D12-22 | implantation (%) | No. of foetuses (%) | |
|---|---|---|---|---|
| | | | total | viable |
| MG132 | 11 | 34 (5.4) | 19 (55.9) | 16* (47.0) |
| control | 11 | 9 (4.1) | 0 | 0 |

*5 living rats at term, 11 living at D12-D14

It is to be noted that under these conditions the rate of implanted embryos that develop into a foetus becomes significantly higher. These foetuses may give rise to viable baby rats (table 4).

Materials and Methods

1. Harvest of Rat Ovocytes

Materials:
Sterile surgical equipment
  1 curved toothed forceps
  2 fine straight forceps
  1 pair of small scissors and one pair of large scissors
  needle (23Gx1")+syringe (5 ml)
Binocular magnifiers+heating stages
Pipettes for manipulation, also used to remove, by aspiration and discharge with the pipette, the crown of cells which at this stage surrounds the ovocyte ("decoronisation")
Petri dishes, 35 and 60 mm diameter
Solutions:
Medium M2 (Hogan & al, 1994 In: Manipulating the Mouse Embryo)
Medium RECMB2*-MG132 (MG132=1.25 µM)
Medium M2-Hyaluronidase-MG132 (MG132=1.25 µM; Hyaluronidase=2.5 mg/ml)
Medium M2-MG132 (MG132=5.00 µM)
*RECMB2=medium mR1ECM-BSA (Oh & al. (1998) Biol. Reprod.), with BSA=4 mg/ml and NaCl=100-130 mM.
Procedure:
The day before harvest:
  turn on the heating stages and put medium M2 and paraffin oil at 37° C.
  prepare the dishes of culture media (RECMB) and place them in the incubator at 37° C., 5% CO2.
1. The dishes used for the harvest of the ovaries-oviducts (M2-MG132 and M2-hyaluronidase-MG132) are prepared with medium and M2 and paraffin oil at 37° C. and are set up on the heating stages at 37° C. at least ½ hour before harvest.
Prepare:
  2 35 mm Petri dishes containing 1.5 to 2 ml of medium M2-MG132 without oil per female.
  1 additional dish of M2 without oil for the rinsing-decoronisation post hyaluronidase.
  1 dish of M2/hyaluronidase with oil for 2 females.
  All dishes are left on the heating stages for the entire duration of the harvest.
2. The rats are sacrificed one by one by cervical dislocation.
3. Pass 70% alcohol over the fur.
4. Do a ventral opening (skin+muscle) by going up the sides by means of the large pair of scissors and the curved back forceps.

5. The ovary and oviduct unit is removed bilaterally as rapidly as possible after sacrifice (approximately 1-2 min) with a second pair of forceps and scissors. Following the uterine tube, go up to the ovary and recover the ovary-oviduct unit. Transfer it into a dish of M2.

6. When the 2 ovary-oviduct units have been recovered, puncture the ampulla of each oviduct with sterile needles mounted on 5 ml syringes to release the cumuli.

7. Harvest the cumuli with a pipetman (P1000) and transfer them either into a second dish of M2 where they can be stored while waiting for the cumuli of the other females to be harvested or into the drop of M2-hyaluronidase-MG132 in the case that the decoronisation is performed immediately.

8. With a pipetman (P1000), transfer the cumuli into a drop of M2-hyaluronidase-MG132 (500 µl). Wait a few seconds for the enzyme to begin to act and then aspirate-discharge the cumuli with the pipette to accelerate their dissociation.

9. Once the cumuli are dissociated, transfer the ovocytes to a dish of M2 (rinsing) and finish "decoronising" them mechanically if the cells of the cumulus are too numerous with the decoronisation pipette:

10. The "decoronised" ovocytes are transferred to a drop of culture medium RECMB2-MG132.

It is necessary to avoid thermal shocks to the ovocytes to the maximum; therefore manipulate quite rapidly and always at 37° C.

2. Production of Embryos by Transfer of the Nucleus of a Donor Cell to the Enucleated Cytoplasm of an Ovocyte Materials:
Inverted microscope with differential interference contrast and x4 and x20 objectives
Right and left Eppendorf motorised micromanipulators
Micromanipulation chamber for the ovocytes and nucleus donor cells
Pipettes for manipulation of the ovocytes
Micropipettes for maintenance of the ovocyte
Micropipettes for enucleation-injection
Piezo-Drill system
Solutions:
Medium M2
Medium RECMB2
Medium RECMB2-MG132 (MG132=1.25 µM)
Medium RECMB2-BLI (BLI=150 µM)
SIGMA light paraffin oil to cover the medium of the culture dishes and of the micromanipulation chamber
SIGMA heavy paraffin oil for the micro-injection system
Fluorinert
Procedure:
All culture media (RECM) with or without drugs are prepared the day before, covered with light paraffin oil and kept in the incubator at 37° C., 5% CO2.

1. Harvest the ovocytes according to the protocol described previously.
2. Assemble the micromanipulation chamber with a fitted coverglass.
3. With the pipetman deposit approximately 500 µl of M2 on the coverglass, forming an elongated drop and cover with light paraffin oil.
4. Fill the enucleation-injection micropipette with Fluorinert from its non-drawn-out end by means of a 1 ml syringe whose needle is connected to a rubber tubing. Take care not to inject air into the micropipette.

Verify that there is enough oil in the injector (Eppendorf syringe). Make some oil flow from the pipette holder before setting up the pipette in order to verify that no air bubble is trapped in the system.

Set up the retention and enucleation-injection pipettes on their respective pipette holders.

5. Position the pipettes so that their ends are horizontal, i.e., parallel to the coverglass of the micromanipulation chamber, and facing each other.
6. Transfer the ovocytes and the cells to the micro-injection chamber by means of a pipette for manipulation of the ovocytes.
7. Maintain an ovocyte on the maintenance pipette in order that the deformation of the plasma membrane under which the ovocyte metaphase is situated, is situated between 2 and 3 hr or between 3 and 4 hr.
8. Apply the enucleation-injection pipette to the pellucid area at 3 hr. Verify that the pipette is in exactly the same plane as the pellucid area. Gently aspirate the pellucid area and activate the piezo system (setting 1) to puncture it. When the system is perfectly adjusted the pellucid area is punctured in a few seconds according to a perfect punch.
9. Next, aspirate a cell whose morphology corresponds to the sought-for criteria into the enucleation-injection pipette and break its plasma membrane by several to-and-fro's in the pipette or by means of the piezo-Drill (a few impulsions are sufficient at setting 2). Maintain the cell close to the end of the micropipette.
10. Penetrate into the perivitelline space of the ovocyte through the previously punctured orifice, apply the pipette against the plasma membrane and push the donor cell back to the end of the pipette and then push the pipette in up to the opposite end of the ovocyte without, however, reaching the plasma membrane opposite.
11. Break the plasma membrane by means of one or more impulsions (1 to 3) of the Piezo-Drill (setting 2).
12. Inject the cell into the cytoplasm of the ovocyte with the minimum possible medium.
13. Gently withdraw the enucleation-injection pipette and re-close the ovocyte by aspirating the 2 ends of the broken plasma membrane and the ovocyte metaphase (enucleation).
14. Transfer the reconstructed embryos into a micro-drop (50 µl) of RECMB2.
15. Ovocyte activation is triggered or prolonged by transfer of the ovocytes to a micro-drop (20 µl) of RECMB2-BLI for a duration of activation generally between 1 and 2 hr.
16. The ovocytes are then rinsed in 4-5 drops (50 µl) of RECMB2 to be cultured in the same medium while waiting to be transferred into a pseudogestating female or to prolong in vitro culture.

REFERENCES

Baguisi et al. (1999) *Nature Biotechnol.* 17, 456-461.
Campbell & al. *Nuclear transfer in practice*, School of Biosciences, University of Nottingham, Leicestershire, United Kingdom.
Chesne et al. (2002) Nature Biotechnol. 20, 366-369.
Hardcastle & al. (2002) Annu. Rev. Pharmacol. Toxicol. 42,325-48.
Hayes & al. (2001) Physiol. Genomics 5, 193-203.
Hee Lee & Goldberg (1998) Trends in Cell Biology 8, 397-403.
Hirabayashi & al. (2003) Cloning and Stem Cells 5(1), 35-41.
Hirabayashi & al. (2003) J. of Reproduction and Development 49(2), 121-6.

Hogan B & al. Recovery, culture and transfer of embryos and germ cells. In: Manipulating the Mouse Embryo: A Laboratory Manual, 2nd ed. Plainview, N.Y.: Cold Spring Harbor Laboratory Press 1994; 173-181.
Iannaccone & al. (2001) Zygote 9, 135-43.
Josefnerg & al. (2000) Biol. Reprod. 62, 1270-77.
Kues W A et al. (2002) Biol. Reprod., 62, 412-419.
Miyoshi et al. (1997) Biol. Reprod. 56, 180-185.
Oh S H et al. (1998) Biol. Reprod. 59, 884-889.
Polejaeva et al. (2000) Nature 407, 86-90.
Pook M A et al. (2001) Neurogenetics, 3, 185-193.
Wakayama et al. (1998) Nature 394, 369-374.
Wells et al. (1999) Biol. Reprod. 60, 996-1005.
Whitfield et al. (1985) Control of Animal Cell Proliferation 1, 331-365.
Wilmut et al. (1997) Nature 385, 810-813.
Zernicka-Goetz M. (1991) Molecular Reproduction and Development 28, 169-76.

The invention claimed is:

1. A method for producing of viable reconstituted rat embryo by nuclear transfer comprising the following steps:
   a) removing a recipient rat ovocyte and maintaining the recipient _ovocyte in vitro in a maintenance medium, wherein the recipient rat ovocyte is maintained at the metaphase stage of the second meiotic division in a maintenance medium including a reversible proteasome inhibitor sufficient to prevent activation of the ovocyte;
   b) transferring the nucleus of a rat donor cell into the recipient rat ovocyte of step a);
   c) removing the recipient rat ovocyte nucleus before or after the introduction of said donor cell nucleus to obtain a reconstituted rat ovocyte; and
   d) activating the reconstituted rat ovocyte by placing the reconstituted ovocyte in an activation medium containing an inducer of activation to obtain a reconstituted rat embryo.

2. The method of claim 1, wherein the reversible proteasome inhibitor is chosen from the group consisting of: Cbz-LLL-H (MG132), peptide boronate Cbz-LLL-B(OH)2, vinyl sulfone Cbz-LLL-Vs, lactacystine and beta-lactone, leupeptine, MG101, MG115, MG262 and PSI (Cbz-ile-glu) and combinations thereof.

3. The method of claim 1, wherein the reversible proteasome inhibitor is MG132.

4. The method of claim 1, wherein the reversible proteasome inhibitor concentration in the medium for maintenance of recipient ovocytes is between 1 and 10 μM.

5. The method of claim 1, wherein the exposure time of the recipient ovocyte to the reversible proteasome inhibitor in the maintenance medium is less than 10 hours, preferably between 1 and 6 hours.

6. The method of claim 1, wherein for nuclear transfer step b), the culture medium of the recipient ovocyte lacks added reversible proteasome inhibitor.

7. The method of claim 1, wherein the nuclear transfer comprises a step for removal of the recipient ovocyte nucleus, followed by a step for introduction of the donor cell nucleus into the enucleated ovocyte.

8. The method of claim 1, wherein the nuclear transfer comprises a step for introduction of the donor cell nucleus into the recipient ovocyte followed by a step for removal of the recipient ovocyte nucleus.

9. The method of claim 7, wherein the transfer of the donor cell nucleus into the cytoplasm of the recipient ovocyte is carried out by micro-injection and or removal of the recipient ovocyte nucleus is carried out by micropipetting.

10. The method of claim 1, wherein the activation medium lacks added reversible proteasome inhibitor.

11. The method of claim 1, wherein the activation inducer is butyrolactone-1.

12. The method of claim 1, wherein said reconstituted embryo is a transgenic embryo.

13. A method for producing of cloned rat foetus by nuclear transfer comprising the following steps:
   a) removing a recipient rat ovocyte and maintaining the recipient_ovocyte in vitro in a maintenance medium, wherein the recipient rat ovocyte is maintained at the metaphase stage of the second meiotic division in a maintenance medium including a reversible proteasome inhibitor sufficient to prevent activation of the ovocyte;
   b) transferring the nucleus of a rat donor cell into the recipient rat ovocyte of step a);
   c) removing the recipient rat ovocyte nucleus before or after the introduction of said donor cell nucleus to obtain a reconstituted rat ovocyte;
   d) activating the reconstituted rat ovocyte by placing the reconstituted ovocyte in an activation medium containing an inducer of activation to obtain an activated reconstituted rat embryo; and
   e) transferring the activated reconstituted embryo into the oviduct or uterus of a recipient female rat wherein said transferred embryo is allowed to become a fetus.

14. The method of claim 13, wherein the reversible proteasome inhibitor is chosen from: Cbz-LLL-H (MG132), peptide boronate Cbz-LLL-B(OH)2, vinyl sulfone Cbz-LLL-Vs, lactacystine and beta-lactone, leupeptine, MG101, MG115, MG262, PSI(Cbz-ile-glu) or combinations thereof.

15. The method of claim 13, wherein the reversible proteasome inhibitor is MG132.

16. The method of claim 13, wherein the reversible proteasome inhibitor concentration in the medium for maintenance of recipient ovocytes is between 1 and 10 μM.

17. The method of claim 13, wherein the exposure time of the recipient ovocyte to the reversible proteasome inhibitor in the maintenance medium is less than 10 hours, preferably between 1 and 6 hours.

18. The method of claim 13, wherein for nuclear transfer step b), the culture medium of the recipient ovocyte lacks added reversible proteasome inhibitor.

19. The method of claim 13, wherein the nuclear transfer comprises a step for removal of the recipient ovocyte nucleus, followed by a step for introduction of the donor cell nucleus into the enucleated ovocyte.

20. The method of claim 13, wherein the nuclear transfer comprises a step for introduction of the donor cell nucleus into the recipient ovocyte followed by a step for removal of the recipient ovocyte nucleus.

21. The method of claim 13, wherein the activation medium lacks added reversible proteasome inhibitor.

22. The method of claim 13, wherein the activation inducer is butyrolactone-1.

23. The method of claim 13, wherein said reconstituted embryo is a transgenic embryo.

24. The method of claim 13, wherein said reconstituted embryo is transferred at the 1 cell stage.

25. The method of claim 13, wherein said reconstituted embryo is transferred at the 2 cells stage.

26. A method for producing a cloned rat by nuclear transfer comprising the following steps:
   a) removing a recipient rat ovocyte and maintaining the recipient_ovocyte in vitro in a maintenance medium, wherein the recipient rat ovocyte is maintained at the metaphase stage of the second meiotic division in a maintenance medium including a reversible proteasome inhibitor sufficient to prevent activation of the ovocyte;

b) transferring the nucleus of a rat donor cell into the recipient rat ovocyte of step a);

c) removing the recipient rat ovocyte nucleus before or after the introduction of said donor cell nucleus to obtain a reconstituted rat ovocyte;

d) activating the reconstituted rat ovocyte by placing the reconstituted ovocyte in an activation medium containing an inducer of activation to obtain an activated reconstituted rat embryo;

e) transferring the activated reconstituted embryo into the oviduct or uterus of a recipient female rat wherein said transferred embryo is allowed to become implanted and to develop into a cloned rat in the uterus of said recipient female; and f) recovering a neonate at birth.

27. The method of claim 26, wherein the reversible proteasome inhibitor is chosen from: Cbz-LLL-H (MG132), peptide boronate Cbz-LLL-B(OH)2, vinyl sulfone Cbz-LLL-Vs, lactacystine and beta-lactone, leupeptine, MG 101, MG115, MG262, PSI(Cbz-ile-glu) or combinations thereof.

28. The method of claim 26, wherein the reversible proteasome inhibitor is MG132.

29. The method of claim 26, wherein the reversible proteasome inhibitor concentration in the medium for maintenance of recipient ovocytes is between 1 and 10 µM.

30. The method of claim 26, wherein the exposure time of the recipient ovocyte to the reversible proteasome inhibitor in the maintenance medium is less than 10 hours, preferably between 1 and 6 hours.

31. The method of claim 26, wherein for step b), the culture medium of the recipient ovocyte lacks added reversible proteasome inhibitor.

32. The method of claim 26, wherein the nuclear transfer comprises a step for removal of the recipient ovocyte nucleus, followed by a step for introduction of the donor cell nucleus into the enucleated ovocyte.

33. The method of claim 26, wherein the nuclear transfer comprises a step for introduction of the donor cell nucleus into the recipient ovocyte followed by a step for removal of the recipient ovocyte nucleus.

34. The method of claim 26, wherein the activation medium lacks added reversible proteasome inhibitor.

35. The method of claim 26, wherein the activation inducer is butyrolactone-1.

36. The method of claim 26, wherein said reconstituted embryo is a transgenic embryo.

37. The method of claim 26, wherein said reconstituted embryo is transferred at the 1 cell stage.

38. The method of claim 26, wherein said reconstituted embryo is transferred at the 2 cells stage.

* * * * *